(12) United States Patent
Kalbag

(10) Patent No.: US 7,326,772 B2
(45) Date of Patent: Feb. 5, 2008

(54) PEPTIDE FOR ASSAYING HERG CHANNEL BINDING

(75) Inventor: Suresh M. Kalbag, Cupertino, CA (US)

(73) Assignee: Penta Biotech, Inc., Union City, CA (US)

( * ) Notice: Subject to any disclaimer, the term of this patent is extended or adjusted under 35 U.S.C. 154(b) by 0 days.

(21) Appl. No.: 11/433,227

(22) Filed: May 11, 2006

(65) Prior Publication Data

US 2006/0275837 A1    Dec. 7, 2006

Related U.S. Application Data

(60) Provisional application No. 60/695,103, filed on Jun. 28, 2005, provisional application No. 60/680,954, filed on May 12, 2005.

(51) Int. Cl.
*C07K 14/00*    (2006.01)
(52) U.S. Cl. .................................................. 530/350
(58) Field of Classification Search ................... None
See application file for complete search history.

(56) References Cited

U.S. PATENT DOCUMENTS

| 6,124,363 | A | 9/2000 | Appleby et al. ............ 514/605 |
| 6,635,452 | B1 | 10/2003 | Monforte et al. .......... 435/91.1 |
| 6,641,997 | B1 | 11/2003 | MacKinnon .................... 435/6 |
| 6,773,886 | B2 | 8/2004 | Kaufman et al. ............... 435/6 |
| 6,824,981 | B2 | 11/2004 | Chait et al. ..................... 435/6 |
| 6,838,291 | B2 | 1/2005 | Liverton et al. ............ 436/504 |
| 2004/0072250 | A1 | 4/2004 | Baranov et al. ............. 435/7.1 |
| 2005/0214870 | A1 | 9/2005 | Greengrass et al. ......... 435/7.2 |

OTHER PUBLICATIONS

Chiu, P.J.S. et al., "Validation of [$^3$H] Astemizole Binding Assay in HEK 293 Cells Expressing HERG-K+ Channels", 2004, J. Pharmacol. Sci. 95, 311-319.
Angelo, K. et al., "A radiolabeled peptide ligand of the hERG channel, [$^{125}$I]-BeKm-1", 2003, Pflugers Arch.-Eur. J. Physiol, 447, 55-63.

*Primary Examiner*—Michael Pak
(74) *Attorney, Agent, or Firm*—Lumen Intellectual Property Services, Inc.

(57) ABSTRACT

The present invention provides compositions and methods useful for assaying binding of compounds to the hERG K$^+$ channel. According to a method of the present invention, a compound of interest is added to the hERG K$^+$ channel in the presence of a selenium analog of a competitive inhibitor of the hERG K$^+$ channel. Next, the amount of the selenium analog of the competitive inhibitor that bound to the hERG K$^+$ channel is quantified using mass spectrometry. The quantified amount can then be used to determine the amount of the compound of interest that bound to the hERG K$^+$ channel. A selenium analog of any competitive inhibitor of the hERG K$^+$ channel may be used according to the present invention, including but not limited to selenium analogs of the small molecule dofetilide; the peptide BeKm-1; or a combination of both.

6 Claims, 5 Drawing Sheets

Di Seleno-Dofetilide

A

Ki of BeKm-1 Analogs in Two Independent FlashBlue Competition Assays.

| Compound | Ki (n=1) | Ki (n=2) | Ki (average) |
|---|---|---|---|
| Biotin-BeKm-1. TFA salt | 5.1 nM | 5.0 nM | 5.1 nM |
| Biotin-BeKm-1. Acetate salt | 2.9 nM | 3.5 nM | 3.2 nM |
| $(SeC)^7$-BeKm-1 TFA salt | 0.18 nM | 0.18 nM | 0.18 nM |
| $(SeC)^7$-BeKm-1 Acetate salt | 0.22 nM | 0.13 nM | 0.18 nM |
| BeKm-1 TFA Salt | 0.43 nM | 0.27 nM | 0.35 nM |

B

A

| Volume % of (SeC)⁷-BeKm-1 solution | Measured Peptide conc. (PPB) in the mixture solution | Measured Se conc. (PPB) in the mixture solution |
| --- | --- | --- |
| 100% | 128.9 | 3.76 |
| 80% | 112.9 | 3.01 |
| 60% | 56.22 | 2.26 |
| 50% | 50.84 | 1.88 |
| 30% | 18.93 | 1.13 |
| 20% | 7.569 | 0.75 |
| 0% | 0 | 0 |

B

[Graph: Se Concentration (PPB) vs Volume % of (SeC)$^7$-BeKm-1 solution; $y = 141.71x - 15.209$; $R^2 = 0.9504$]

FIG. 5

```
                              SEQUENCE LISTING

<160> NUMBER OF SEQ ID NOS: 1

<210> SEQ ID NO 1
<211> LENGTH: 36
<212> TYPE: PRT
<213> ORGANISM: Buthus eupeus

<400> SEQUENCE: 1

Arg Pro Thr Asp Ile Lys Cys Ser Glu Ser Tyr Gln Cys Phe Pro Val
1               5                  10                  15

Cys Lys Ser Arg Phe Gly Lys Thr Asn Gly Arg Cys Val Asn Gly Phe
            20                  25                  30

Cys Asp Cys Phe
            35
```

PEPTIDE FOR ASSAYING HERG CHANNEL BINDING

CROSS-REFERENCE TO RELATED APPLICATION

This application claim priority from U.S. Provisional Application No. 60/680,954, filed May 12, 2005, and U.S. Provisional Patent Application No. 60/695,103, filed Jun. 28, 2005, both of which are incorporated herein by reference.

FIELD OF THE INVENTION

The present invention related generally to drug discovery. More particularly, the present invention related to composition and methods useful for assaying binding of compound to the hERG (Human Ether-a-go-go Related Gene) $K^+$ channel.

BACKGROUND

Voltage-dependant ion channels are proteins that span cell surface membranes in excitable tissue such as heart and nerves. Ions passing through channels form the basis of the cardiac action potential. Influx of $Na^+$ and $Ca^{2+}$ ions, respectively, control the depolarizing upstroke and plateau phases of the action potential. $K^+$ ion efflux repolarizes the cell membrane, terminates the action potential, and allows relaxation of the muscle. A rapid component of the repolarizing current flows through the K+ channel encoded by the human ether-a-go-go-related gene (hERG). Impaired repolarization can prolong the duration of the action potential, delay relaxation and promote disturbances of the heartbeat. Action potential prolongation is detected clinically as a lengthening of the QT interval measured on the electrocardiogram (ECG).

Drug-induced QT prolongation is a serious complication of drugs due to impaired repolarization, which is associated with an increased risk of lethal ventricular arrhythmias. Drug-induced QT prolongation is almost always associated with block of the hERG $K^+$ channel. A plethora of drugs, such as methanesulfonanilides, dofetilide, MK-499, and E-4031 are known to block $K^+$ ion channels such as hERG on the heart causing a life threatening ventricular arrhythmia and heart attack in susceptible individuals. Unfortunately, incidence of drug-induced ventricular arrhythmia is often too low to be detected in clinical trials.

A sudden death due to the blocking of hERG channels by noncardiovascular drugs such as terfenadine (antihistamine), astemizole (antihistamine), and cisapride (gastrokinetic) led to their withdrawal from the market. Recently, drugs like Vioxx, Celebrex and Bextra were also pulled out of the market for concerns relating to dangerous cardiac side effects. Consequently, cardiac safety relating to $K^+$ channels has become a major concern of regulatory agencies. In order to prevent costly attrition, it has therefore become a high priority in drug discovery to screen out inhibitory activity on hERG channels in lead compounds as early as possible.

Current methods for testing potential drug molecules for hERG blocking activity have several limitations. Technologies based on cell-based patch clamp electrophysiology or animal tests are technically difficult and do not meet the demand for throughput and precision for preclinical cardiac safety tests. Other assays use radio-labeled, fluorescent, dye-conjugated, or biotinylated markers for detection and quantification of binding. However, many of these markers have reduced activity after labeling. In addition, the use of radio-labeled analogs poses practical limitations such as requirements for complex infrastructure and licenses for operating radioactive compounds. Accordingly, there is a need in the art to develop new compositions and methods for quantifying the binding of drug molecules to hERG channels.

SUMMARY OF THE INVENTION

The present invention provides compositions and methods useful for assaying binding of compounds to the hERG $K^+$ channel. According to a method of the present invention, a compound of interest is added to the hERG $K^+$ channel in the presence of a selenium analog of a competitive inhibitor of the hERG $K^+$ channel. Next, the amount of the selenium analog of the competitive inhibitor that bound to the hERG $K^+$ channel is quantified using mass spectrometry. The quantified amount can then be used to determine the amount of the compound of interest that bound to the hERG $K^+$ channel.

A selenium analog of any competitive inhibitor of the hERG $K^+$ channel may be used according to the present invention, including but not limited to selenium analogs of the small molecule dofetilide; the peptide BeKm-1, the sequence of which is shown in SEQ ID NO:1; or a combination of both. BeKm-1 is a 36 amino acid peptide isolated from the Central Asian scorpion *Buthus eupeus* that strongly binds to the hERG $K^+$ channel. Preferably, the selenium analog of the competitive inhibitor has a $K_i$ within an order of magnitude of the $K_i$ of an unmodified version of the competitive inhibitor, more preferably within about 3 times the $K_i$ of an unmodified version of the competitive inhibitor.

In a preferred embodiment, the amount of competitive inhibitor that bound to the hERG $K^+$ channel is quantified by quantifying the amount of selenium that bound to the hERG $K^+$ channel. This can be accomplished using any type of mass spectrometry, including but not limited to matrix assisted laser desorption time of flight (MALDI-TOF) mass spectrometry, electrospray mass spectrometry, and inductively coupled plasma mass spectrometry (ICP-MS).

The present invention also provides selenium analogs of competitive inhibitors of the hERG $K^+$ channel. In one embodiment, at least one cysteine of BeKm-1 is replaced with seleno-cysteine. In one aspect of this embodiment, the seventh residue, cysteine, of BeKm-1 is replaced with seleno-cysteine to form $(SeC)^7$-BeKm-1. In another embodiment, methyl-seleno-cysteine is covalently bonded to the first amino acid of BeKm-1 to form $(MeSeC)^0$-BeKm-1. In yet another embodiment, the selenium analog is di-seleno-dofetilide. Preferably, the selenium analogs of BeKm-1 have $K_i$s for the hERG $K^+$ channel in the range of about 0.08 nM to about 1.0 nM. Also preferably, di-seleno-dofetilide has a $K_i$ for the hERG $K^+$ channel in the range of about 4 nM to about 25 nM. The present invention also includes pharmaceutically acceptable salts of the above selenium analogs, including but not limited to acetate, TFA, maleate and hydrochloride salts.

BRIEF DESCRIPTION OF THE FIGURES

The present invention together with its objectives and advantages will be understood by reading the following description in conjunction with the drawings, in which:

FIG. 5 shows detection of selenium in $(SeC)^7$-BeKm-1 by mass spectrometry according to the present invention.

DETAILED DESCRIPTION OF THE INVENTION

The present invention provides methods of detecting binding of a compound of interest to the hERG $K^+$ channel. In a first step, a selenium analog of a competitive inhibitor of the hERG $K^+$ channel is added along with the compound of interest to the hERG $K^+$ channel. The hERG $K^+$ channel may be presented to the compounds in any form, including but not limited to as purified protein on a protein chip, expressed on the surface of cells, or from membranes prepared from hERG $K^+$ channel-expressing cells. In the latter two cases, the hERG $K^+$ channel could be presented in, for example, a 96-well plate format. According to the present method, bound competitive inhibitor is quantified using mass spectrometry (MS). This is possible by using the mass spectrometer to detect the presence and amount of selenium. Selenium is an element not found in the hERG $K^+$ channel. Thus, as long as the compound of interest does not contain selenium, the amount of bound competitive inhibitor can be directly related to the amount of selenium present in the mixture.

The assay may be used to quantify the amount of selenium in two basic ways. With the first method, a solution of the compound of interest and a solution of the competitive inhibitor would be added to the hERG $K^+$ channel and incubated for an appropriate period of time. At the end of the incubation period, the supernatant would be transferred from the assay and diluted into an appropriate volume. The diluted supernatant would then be injected into a mass spectrometer, selenium would be detected, and these values would be used to determine the amounts of the competitive inhibitor and the compound of interest that bound to the hERG $K^+$ channel. With this method, an increase of selenium concentration in the supernatant compared to assays with competitive inhibitor only (i.e. without any additional compound of interest) would correspond to a reduction of binding of the competitive inhibitor to the hERG $K^+$ channel, and would indicate binding of the compound of interest to the hERG $K^+$ channel.

With the second method, at the end of the incubation period, the hERG $K^+$ channel would be washed to remove unbound material and bound competitive inhibitor would be released using, e.g., an appropriate denaturant. The denatured mixture would then be diluted in an appropriate volume and injected into a mass spectrometer. Selenium would be detected and these values would be used to determine the amount of competitive inhibitor bound and the amount of the compound of interest that bound to the hERG $K^+$ channel. With this method, a decrease in selenium concentration compared to assays with competitive inhibitor alone would correspond to a decrease in bound competitive inhibitor, indicating that the compound of interest bound the hERG $K^+$ channel. With either method, the peak area of the selenium-containing daughter ion in the absence of any compound of interest would serve as the control selenium value.

Daughter ions may be produced from the mixture for MS analysis in several different ways, including but not limited to using electrospray ionization, matrix-assisted laser desorption/ionization (MALDI), and inductively coupled plasma (ICP) sources. The daughter ions may then be separated using any type of MS, including but not limited to time-of-flight (TOF) MS. Selenium-containing daughter ions can then be detected due to their unique mass-to-charge ratios. ICP-MS is particularly well suited to this method, as it specifically detects metals such as selenium at a very low concentration.

The competitive inhibitor may be a selenium analog of any molecule that binds to the hERG $K^+$ channel. Examples include selenium analogs of the BeKm-1 peptide and dofetilide and combinations thereof. Preferably, the selenium analog of the competitive inhibitor has a $K_i$ within an order of magnitude of the $K_i$ of an unmodified version of the competitive inhibitor, more preferably within about 3 times the $K_i$ of the unmodified version. This will ensure adequate sensitivity of the assay.

In one embodiment, the competitive inhibitor is a selenium analog of the peptide BeKm-1. The native amino acid sequence of BeKm-1 is RPTDI KCSES YQCFP VCKSR FGKTN GRCVN GFCDCF (SEQ ID NO:1). In one aspect of this embodiment, at least one cysteine in the native sequence is replaced with seleno-cysteine. In one example, referred to hereafter as $(SeC)^7$-BeKm-1, the seventh residue of the BeKm-1 peptide, a cysteine, is replaced with seleno-cysteine. This modified peptide is well suited for this assay as selenium is not found in the hERG receptor, and is not likely to be found in the molecule of interest. Thus, the only source of selenium would be from the competitive inhibitor. In addition, selenium is chemically similar to sulfur, forming an S—Se bond similar to a disulfide bond, resulting in minimal changes to the structure of the native BeKm-1 peptide.

$(SeC)^7$-BeKm-1 can be made with solid phase synthesis techniques using Boc-Phe-PAM (Butyloxycarbonyl-Phenylalanine-Phenylacetamidomethyl) polystyrene resin and Boc (Butyloxycarbonyl)-protected amino acid derivatives (FIG. 1). First, Boc-Phe-PAM is deprotected by removal of the Boc group (step 110). Next, after neutralization and checking of the amine bond, Boc-(pMB)Cys, the Boc derivative of the next amino acid in the peptide sequence, is coupled to Phe-PAM (step 120). The amine bond is then checked and Boc-(pMB)Cys is recoupled if necessary. This cycle is then repeated with each amino acid derivative corresponding to the sequence in backward order until residue 8 (Ser) is reached (step 130). Boc-(pMB)Se-Cys is then coupled to the peptide and deprotected (step 140) and synthesis is completed through the first residue in the peptide (Arg) (step 150). The completed peptide is then cleaved from the resin using HF (step 160). The HF is then removed, the resin is extracted with 50% ACN/H2O (0.1% TFA) and the peptide is diluted to <1 mM. The pH of the peptide solution is then adjusted to between about 7 and 7.5, folding is performed overnight, with folding monitored by high pressure liquid chromatography (HPLC), and the peptide is purified using HPLC (step 170).

In another aspect of this embodiment, methyl-seleno-cysteine is attached to the N-terminal Arg residue of BeKm-1 to produce $(MeSeC)^0$-BeKm-1. $(MeSeC)^0$-BeKm-1 can be made using solid phase synthesis techniques, again using Boc-Phe-PAM polystyrene resin and Boc-protected amino acid derivatives (FIG. 2). In this case, the peptide is synthesized all the way up to the first residue, Arg (step 210). Boc-Methyl-Se-Cys is then coupled to the peptide (step 220) and deprotected (step 230). The completed peptide is then cleaved from the resin with HF (step 240) and the peptide is diluted to <1 mM. The HF is then removed, the resin is extracted with 50% ACN/H2O (0.1% TFA) and the peptide is diluted to <1 mM. The pH of the peptide solution is then adjusted to between about 7 and 7.5, folding is performed overnight, with folding monitored by high pressure liquid chromatography (HPLC), and the peptide is purified using HPLC (step 250).

Figure 1:
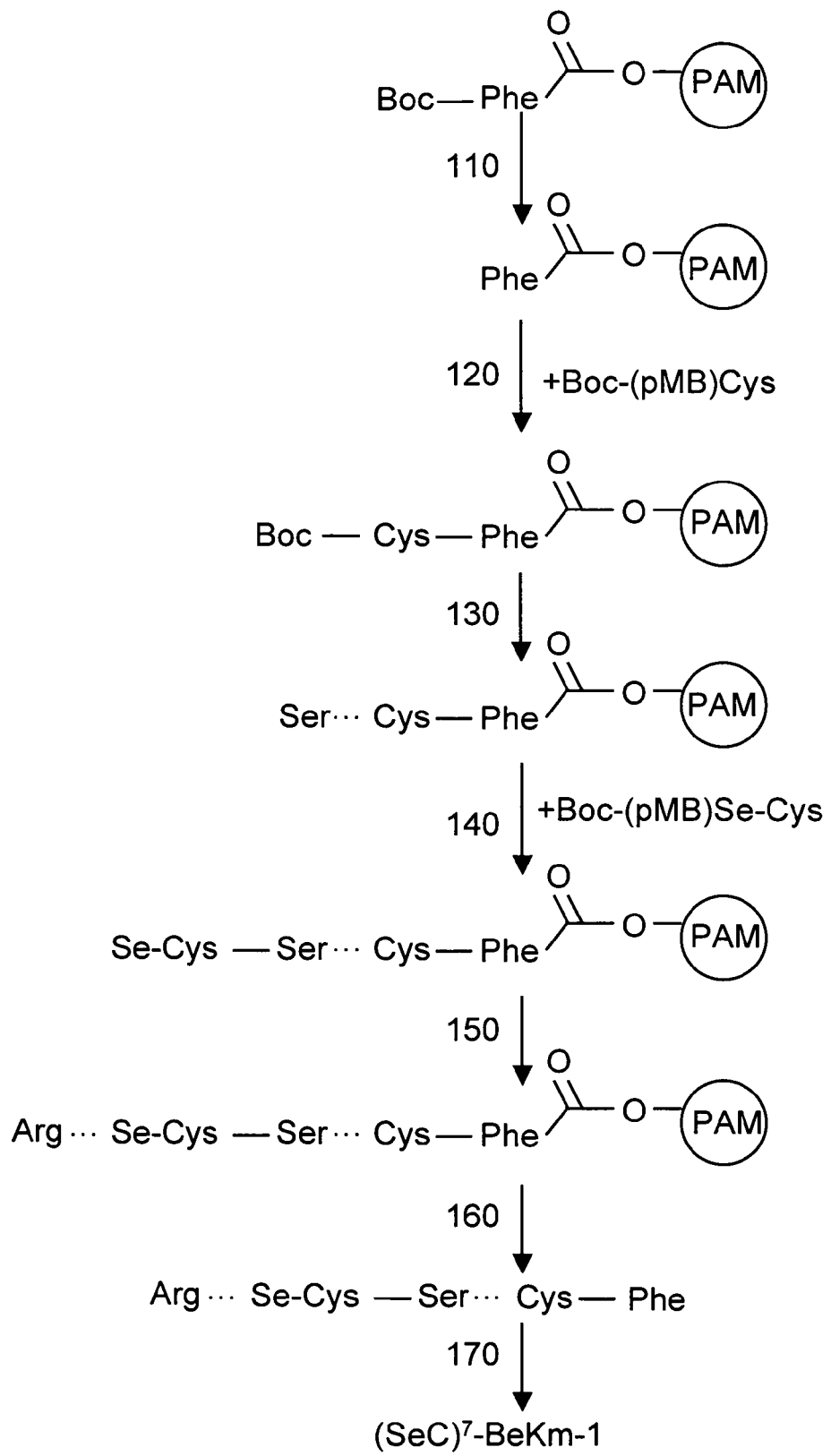
FIG. 1 shows a schematic of synthesis of $(SeC)^7$-BeKm-1 according to the present invention.
Figure 2:
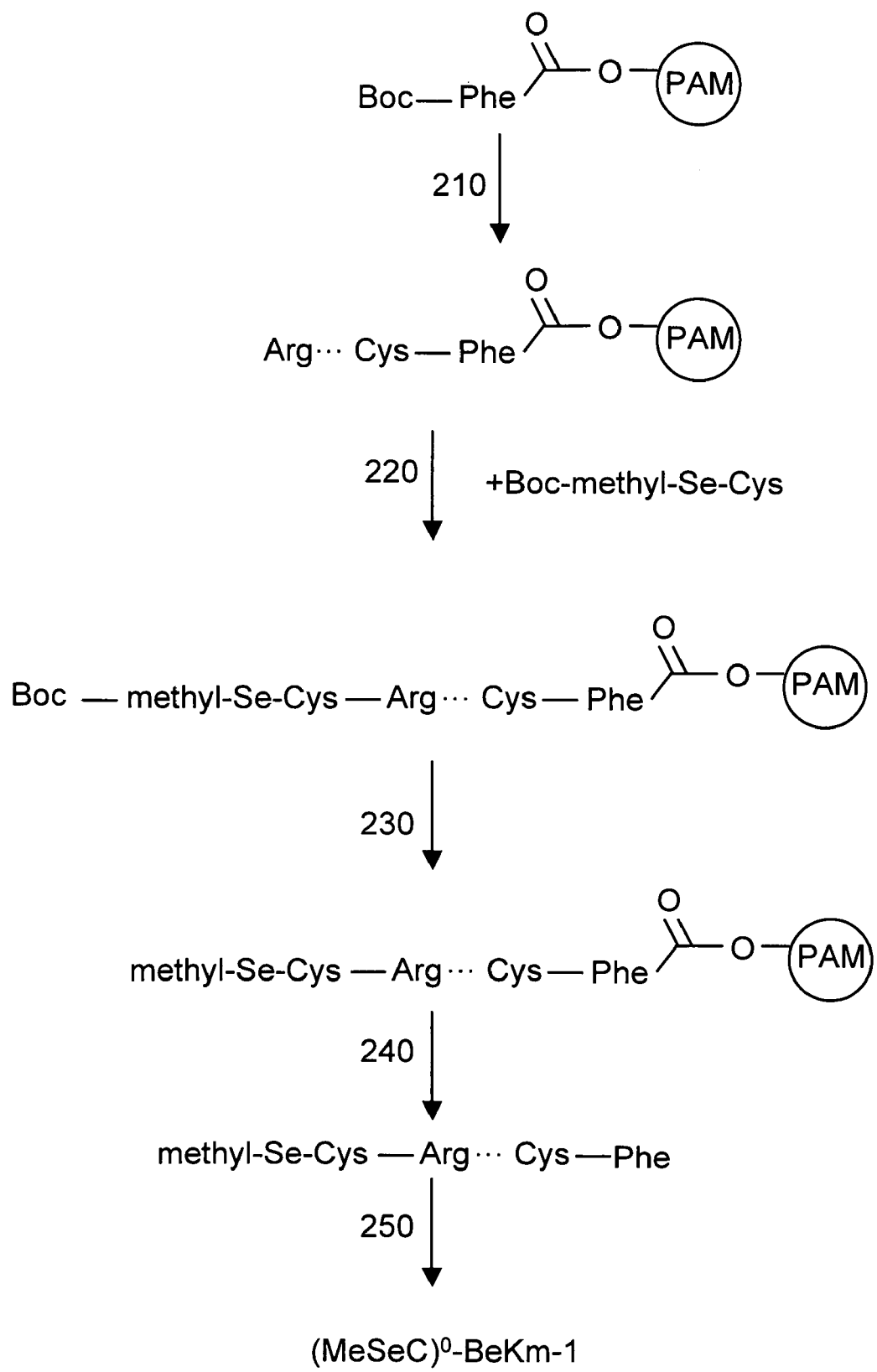
FIG. 2 shows a schematic of synthesis of $(MeSeC)^0$-BeKm-1 according to the present invention.
Figure 3:
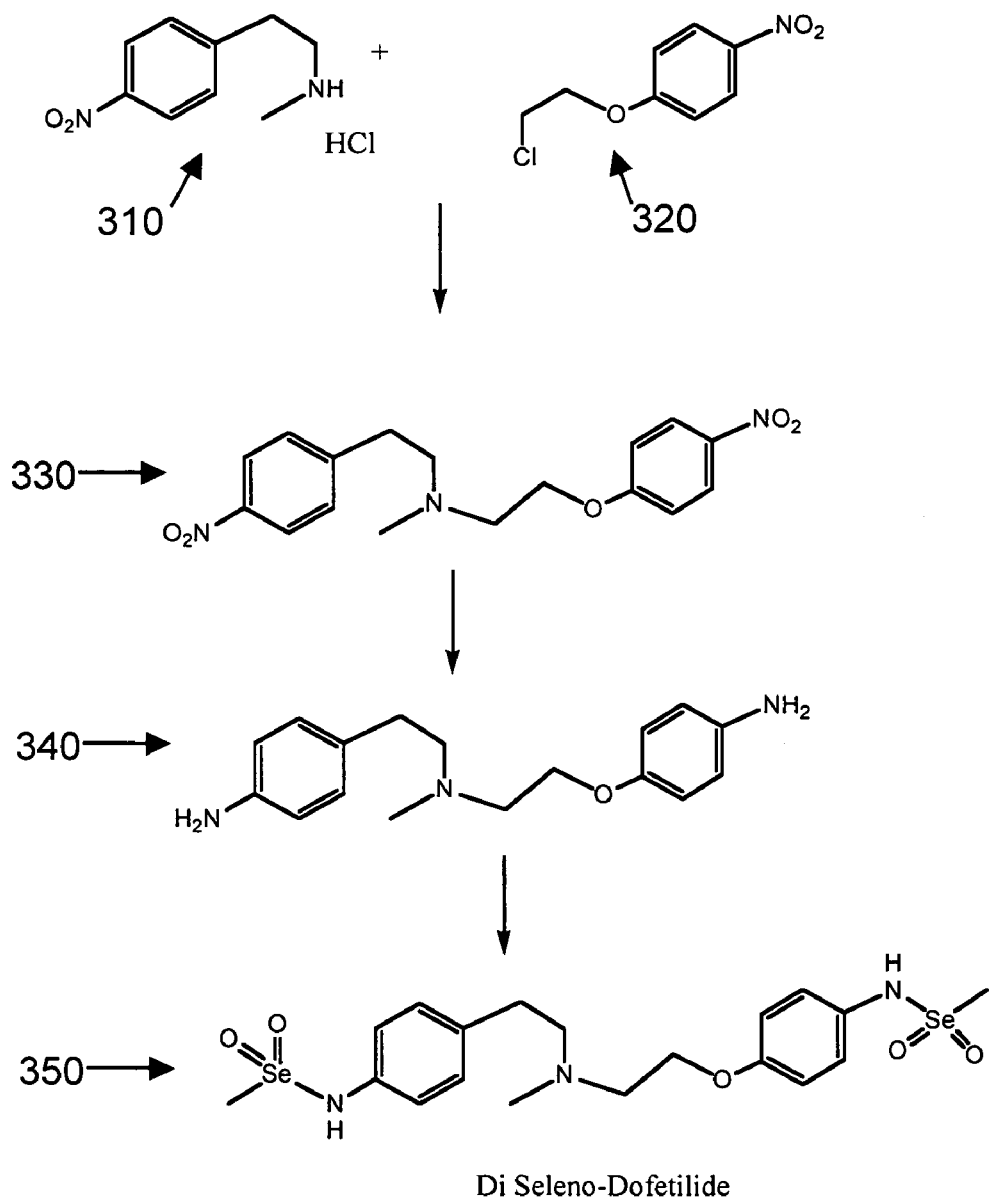
FIG. 3 shows a schematic of synthesis of di-seleno-dofetilide according to the present invention.
Figure 4:
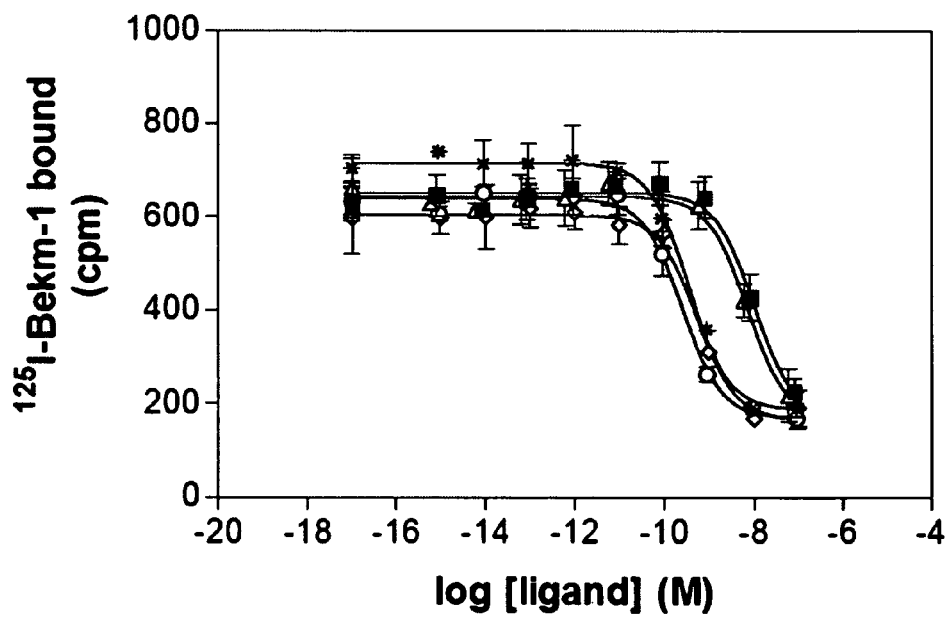
FIG. 4 shows the results of FlashBlue competition assays for BeKm-1 analogs according to the present invention.

In another embodiment, the competitive inhibitor is a selenium analog of dofetilide (N-[4-(2-[2-[4-(methane-sulphonamido)phenoxy]-N-methylethylamino]ethyl)phenyl]methane-sulfphonamide). In one aspect of this embodiment, the selenium analog is di-seleno-dofetilide(n-[4-(2-[2-[4-(methaneselenodoioxamido)phenoxyl]-N-methylethylamino)ethyl)phenyl]-methane-selenodioxamide). Di-seleno-dofetilide may be synthesized according to the scheme shown in FIG. 3, which is based on the synthesis of dofetilide described in U.S. Pat. No. 6,124,363. First, N-methyl-2-(4-nitrophenyl)ethylamine hydrochloride (compound 310) is mixed with 4-(2-chloroethoxy) nitrobenzene (compound 320), anhydrous potassium carbonate, potassium iodide, tetra-n-butylammonium iodide and deionized water and heated under reflux for 3 hours. Next, the mixture is cooled to about 40° C., ethyl acetate is added, and the mixture is extracted with ethyl acetate and concentrated. Ethanol is then added to the extract to precipitate the product and the product is filtered to give N-Methyl-N-[2-(4-nitrophenoxy)ethyl]-4-nitrophenethylamine (compound 330). In the next step, compound 330 and 5% w/v palladium-on-carbon are added to methanol, stirred and hydrogenated at 60 p.s.i. to give N-Methyl-N-[2-(4-aminophenoxy)ethyl]-4-aminophethylamine (compound 340). Compound 340 is then added to acetonitrile, followed by triethylamine and methaneselenodioxy chloride. Sodium carbonate is then added to the reaction mixture and distilled. Next, sodium hydroxide is added to the mixture, followed by concentrated hydrochloric acid. The solid is the collected by filtration, washed with water, and dried to obtain di-seleno-dofetilide (compound 350).

BeKm-1 is thought to interact mostly with closed channels and block K+ current by interacting with the hERG channel's outer vestibule. In contrast, dofetilide is believed to interact with open and/or inactivated hERG channels, accessing the channel's vestibule from the inside of the cell. Thus, in one embodiment, selenium analogs of both BeKm-1 and dofetilide are used to assay a compound of interest for its ability to bind to the hERG channel. The two analogs could be used in separate experiments or combined into one experiment.

EXAMPLES

Synthesis of Selenium Analogs of BeKm-1

Materials and Methods

Boc-Phenylalanyl-O-methyl-PAM resin (Loading: 0.67 mmoles of Boc-Phe/g resin) was bought from Peninsula Labs (Bachem, Inc.). Most Boc amino acids, including Boc-S (pMB)-Cysteine, HOBT (N-hydroxybenzotriazole) and HBTU (2-[1H-Benzotriazole-1-yl]-1,1,3,3-tetramethylaminium hexafluorophosphate) were bought from Peninsula Labs. Boc-Asparagine (Xan)-OH and Boc-Glutamine (Xan)-OH were bought from EMD Biosciences. SelenoCystine.2 HCl and Methyl Seleno-Cysteine were bought from Sabinsa Corporation and were converted to Boc-(Se-pMB)-Cysteine and Boc-Methyl-Seleno-cysteine respectively. Ethyldiisopropyl amine (DIEA) and Diisopropyl Carbodiimide (DIC) were purchased from Sigma-Aldrich.

Synthesis of pMethylbenzyl Seleno-Cysteine

Seleno-Cystine.2 HCl (31.2 mmoles, 10.6 g) was mixed with about 100 mL of 0.5 N NaOH to make a slurry. A solution of Sodium Borohydride (10 g, 253 mmoles) in water (60 mL) was added dropwise to the well-stirred solution of Seleno-Cystine in a 500 mL round bottom flask, which was well chilled to prevent boiling. After the vigorous reaction, the solution turns from yellow to colorless. Glacial acetic acid was added until the pH was approximately 6 (~20 mL). 2-Methylbenzyl Bromide (8.5 mL, 63 mmoles) was added dropwise to the above solution. The reaction was completed in about 30 minutes. The solution was acidified with concentrated HCl to pH 3 to complete the formation of the precipitate. The precipitate was filtered after letting it stand overnight and was dissolved in 200 mL boiling water. After letting it stand in the refrigerator for 3 hours, the crystals were filtered, washed with water and then dried. The yield was 10 g.

Synthesis of Boc-Se (pMB)-Cysteine pMethylbenzyl (pMB) Seleno-Cysteine. HCl (9 g, 33.3 mmoles) was mixed with water (90 mL) to make a slurry in a one-liter flask. After adding triethylamine (TEA) (4.7 mL, 33.3 mmoles) to the slurry at room temperature while stirring, a solution of $(Boc)_{2O}$ or di-tert-butyl carbonate (14.5 g, 66.6 mmoles) in acetonitrile (100 mL) was added and an additional amount of TEA (4.7 mL, 33.3 mmoles) was added. The solution became clear. The reaction was stirred at room temperature for an additional hour, after which it was acidified with 1 N HCl (45 ML). It was then extracted with ethyl acetate. The ethyl acetate extract was washed with 1 N HCl (3×100 mL) and the aqueous layer was again extracted with ethyl acetate. This extract was combined with the first extract, dried over anhydrous $Na_2SO_4$ and evaporated to dryness using a Rotovap. Yield: 8.0 g Synthesis of Boc-(methyl)-Seleno-Cysteine Methyl-Seleno-Cysteine. HCl (6.21 g, 33.3 mmoles) was mixed with water (90 mL) to make a slurry in a one-liter flask. After adding TEA (4.7 mL, 33.3 mmoles) to it, at room temperature with good stirring, a solution of (Boc) 20 or di-tert-butyl carbonate (14.5 g, 66.6 mmoles) in acetonitrile (100 mL) was added to it and an additional amount of TEA (4.7 mL, 33.3 mmoles) was added. The solution became clear. The reaction was stirred at room temperature for an additional hour, after which it was acidified with 1 N HCl (45 ML). It was then extracted with ethyl acetate. The ethyl acetate extract was washed with 1 N HCl (3×100 mL). The aqueous layer was then extracted again with ethyl acetate. This extract was combined with the first extract, dried over anhydrous $Na_2SO_4$ and evaporated to dryness using a Rotovap. Yield: 7 g Synthesis of BeKm-1

Boc (Tos) Arg[1]-Pro-(Bzl) Thr-(Cyh) Asp-Ile-(ClZ) Lys-S (pMB) Cys[7]-(Bzl) Ser-(Cyh) Glu-(Bzl) Ser[10]-(BrZ) Tyr-Gln-(pMB) Cys-Phe-Pro[15]-Val-(pMB) Cys-(ClZ) Lys-(Bzl) Ser-(Tos) Arg[20]-Phe-Gly-(ClZ) Lys-(Bzl) Thr-Asn[25]-Gly-(Tos) Arg-(pMB) Cys-Val-Asn[30]-Gly-Phe-(pMB) Cys-(Cyh) Asp-(pMB) Cys[35]-Phe-PAM-resin.

Using Boc protected amino acids and general Boc chemistry the above sequence was synthesized on Boc-Phe-O-methyl PAM resin. Generally the method of choice for coupling amino acid residues was using DIC/HOBT. When some amino acids needed to be double coupled, HBTU and DIEA were used for the second coupling. The completion of couplings was checked by the Kaiser test.

Synthesis of $(SeC)^7$-BeKm-1

Boc (Tos) $Arg^1$-Pro-(Bzl) Thr-(Cyh) Asp-Ile-(ClZ) Lys-(pMB) $SeCys^7$-(Bzl) Ser-(Cyh) Glu-(Bzl) $Ser^{10}$-(BrZ) Tyr-Gln-(pMB) Cys-Phe-$Pro^{15}$-Val-(pMB) Cys-(ClZ) Lys-(Bzl) Ser-(Tos) $Arg^{20}$-Phe-Gly-(ClZ) Lys-(Bzl) Thr-$Asn^{25}$-Gly-(Tos) Arg-(pMB) Cys-Val-$Asn^{30}$-Gly-Phe-(pMB) Cys-(Cyh) Asp-(pMB) $Cys^{35}$-Phe-PAM-resin Using Boc protected amino acids and general Boc chemistry the above sequence was synthesized on Boc-Phe-O-methyl PAM resin. The synthesis was performed using the same strategy as mentioned above, except for the residue seven, where Boc-Se (pMB)-Cysteine was used. The same coupling strategy was used as that used for the BeKm-1 synthesis. The coupling efficiency was checked using the Kaiser test.

Synthesis of $(MeSeCys)^0$-BeKm-1

Boc $MeSeCys^0$-Boc (Tos) $Arg^1$-Pro-(Bzl) Thr-(Cyh) Asp-Ile-(ClZ) Lys-(pMB) $SeCys^7$-(Bzl) Ser-(Cyh) Glu-(Bzl) $Ser^{10}$-(BrZ) Tyr-Gln-(pMB) Cys-Phe-$Pro^{15}$-Val-(pMB) Cys-(ClZ) Lys-(Bzl) Ser-(Tos) $Arg^{20}$-Phe-Gly-(ClZ) Lys-(Bzl) Thr-$Asn^{25}$-Gly-(Tos) Arg-(pMB) Cys-Val-$Asn^{30}$-Gly-Phe-(pMB) Cys-(Cyh) Asp-(pMB) $Cys^{35}$-Phe-PAM-resin Boc-Phenylalanyl-O-methyl-PAM resin was used with a loading of 0.67 mmoles of Boc Phe/gm of resin. The synthesis was performed similar to the regular BeKm-1 using the same strategy as mentioned above. However, after the completion of the sequence for BeKm-1, Boc-methyl-Seleno-Cysteine was coupled to the residue 1. The same coupling strategy was used as that used for the BeKm-1 synthesis. The coupling efficiency was checked using the Kaiser test.

Method of Cleavage from the Resin and Folding:

For all three peptide resins the following method was used.

i) Removal of Boc Protection:

The resin was initially treated with 50% TFA/DCM to remove the Boc group, washed with DCM, DMF and Ether and dried.

ii) HF Cleavage:

The dry resin was transferred to a HF reaction vessel and p-Cresol was added (1 ml/g resin). Liquid Hydrogen Fluoride (10 ml/g peptide resin) was added to the reaction vessel, and the reaction was cooled in dry ice/acetone and evacuated with high vacuum. The resin was stirred at 0° C. for 1 hour. The HF was then removed at 0° C. under vacuum. The resin was extracted with a mixture of buffer B (0.1% TFA/ACN) and buffer A (0.1% TFA/$H_2O$), after washing thoroughly with anhydrous Ether.

iii) Folding:

The peptide solution was diluted with deionized water to 0.5 mM (or possibly more as long as the percentage of ACN was not less than 10% after dilution), pH was adjusted to 7-7.5 and the solution was stirred at room temperature overnight. The progress of folding was monitored by HPLC. The folding was complete by the next morning. The pH was then reduced to 4 by adding acetic acid.

iv) Purification:

The solution was centrifuged to remove some insoluble material. The solution was then loaded onto a Hamilton PRP-1 column (25×250 mm; 10 mm beads) using a Rainin Dynamax HPLC machine. The following conditions were used; Buffer A: 0.1% TFA/water; Buffer B: 0.1% TFA in acetonitrile, Flow Rate: 40 mL/min., Wavelength of detection: 230 nm. Gradient: 10 to 40% B in 80 min.

The fractions with the right mass were pooled and lyophilized.

The lyophilized peptide was then loaded onto a Phenomenex "Luna (2)" (C18, 10 mm, 100 A, 1") column with the same buffer system and gradient that was used earlier but at a flow rate of 9 mL/min and wavelength of detection at 230 nm. The analytical runs were done on a Luna (2), 5 mm, 100 A, 4.6×250 mm, C18 column on an Agilent 1100 HPLC system, with the same buffer system at 1 mL/min flow rate, UV 210 nm and gradient 10-40% B in 100 min. The fractions were collected and, based upon the analytical runs and the mass spectra, the fractions containing the right molecular weight material and right purity were pooled and lyophilized.

Flash Blue Competition Assays with BeKm-1 Analogs

Acetate and TFA salts of $(SeC)^7$-BeKm-1 were tested in homogeneous $[^{125}I]$-BeKm-1 competition assays using FlashBlue GPCR beads and hERG $K^+$ channel membranes derived from Perkin Elmer's hERG/HEK-293 cell line (clone 16). Radioligand was used at the $K_d$ concentration determined for the FlashBlue assay (0.17 nM). Assays were run in buffer composed of 20 mM Hepes/Tris pH 7.2, 100 μM KCl, 0.5% BSA. 1.25 μg hERG $K^+$ channel membranes and 62.5 μg FlashBlue GPCR beads were added to each well of a 384-well white Optiplate. The total assay volume for each well was 40 μl. Plates were spun briefly after a one hour incubation at room temperature prior to signal detection with a TopCount apparatus.

The results of the assays are shown in FIG. 4. FIG. 4A is a summary of $K_i$ values of $(SeC)^7$-BeKm-1 in comparison to native BeKm-1 and Biotinylated BeKm-1. FIG. 4B is an example of data obtained from a FlashBlue experiment. In FIG. 4B, the closed rectangles show results for biotinyl-BeKm-1 TFA salt; open triangles are biotinyl-BeKm-1 acetate salt; stars are $(SeC)^7$-BeKm-1 TFA salt; open circles are $(SeC)^7$-BeKm-1 acetate salt; and open diamonds are BeKm-1 TFA salt. FIG. 4 shows that $(SeC)^7$-BeKm-1 analogs have an affinity for the hERG channel comparable to that of native BeKm-1. By comparison, biotinylated analogs of BeKm-1 have an affinity that is shifted by about one log to the right.

ICP-MS Quantitation of $(SeC)^7$-BeKm-1

ICP-MS analysis was performed, using standard protocols, on a mixture of 0.2 mg/L of $(SeC)^7$-BeKm-1 in dilute acetic acid solution and 1 mM of Celebrex in dilute acetate solution at different proportions (%). FIG. 5A shows a table and FIG. 5B shows a graph of the results of this analysis. FIG. 5 shows that bound competitive inhibitor can be measured even when the competitive inhibitor solution only makes up 20% of the total volume analyzed. Selenium from the competitive inhibitor can be detected at a concentration of 0.75 parts per billion, corresponding to a peptide concentration of 7.569 parts per billion.

As one of ordinary skill in the art will appreciate, various changes, substitutions, and alterations could be made or otherwise implemented without departing from the principles of the present invention. For example, selenium analogs of astemizole, terfenadine, or any other hERG $K^+$ channel blocker may be useful according to the present invention. Accordingly, the scope of the invention should be determined by the following claims and their legal equivalents.

What is claimed is:

1. A peptide comprising a variant of the sequence SEQ ID NO:1, wherein at least one cysteine of the sequence SEQ ID NO:1 is replaced with seleno-cysteine in the sequence of said peptide, and wherein the remainder of said sequence of said peptide is identical to SEQ ID NO:1.

2. The peptide as set forth in claim 1, wherein the cysteine at amino acid number seven of the sequence SEQ ID NO:1 is replaced with seleno-cysmeine in the sequence of said peptide.

3. The peptide as set forth in claim 1, wherein said peptide binds hERG $K^+$ channel with a $K_i$ in the range of about 0.08 nM to about 1.0 nM.

4. The peptide as set forth in claim 1, wherein said peptide binds hERG $K^+$ channel with a $K_i$ of about 0.2 nM.

5. A peptide comprising a variant of the sequence SEQ ID NO:1, wherein said peptide has methyl-seleno-cysteine covalently bonded to the first amino acid of SEQ ID NO:1, and wherein the remainder of the sequence of said peptide is identical to SEQ ID NO:1.

6. The peptide as set forth in claim 5, wherein said peptide binds hERG $K^+$ channel with a $K_i$ in the range of about 0.08 nM to about 1.0 nM.

* * * * *